United States Patent [19]

Gillig et al.

[11] Patent Number: 5,481,003

[45] Date of Patent: Jan. 2, 1996

[54] PROTEIN KINASE C INHIBITORS

[75] Inventors: James R. Gillig; Michael R. Jirousek, both of Indianapolis, Ind.

[73] Assignee: Eli Lilly and Company, Indianapolis, Ind.

[21] Appl. No.: 263,912

[22] Filed: Jun. 22, 1994

[51] Int. Cl.$^6$ .................... C07D 403/04; C07D 403/14; A61K 31/40; A61K 31/415
[52] U.S. Cl. ........................... 548/455; 548/312.1
[58] Field of Search ................... 548/455, 312.1; 514/414, 397

[56] References Cited

U.S. PATENT DOCUMENTS

| | | | |
|---|---|---|---|
| 4,923,986 | 5/1990 | Murakata et al. | 540/545 |
| 5,057,614 | 10/1991 | Davis et al. | 548/466 |

FOREIGN PATENT DOCUMENTS

| | | | |
|---|---|---|---|
| 3914764A1 | 11/1990 | Denmark | 403/14 |
| 0434057A2 | 12/1990 | Denmark | 487/14 |
| 0269025A2 | 11/1987 | European Pat. Off. | 19/44 |
| 0470490A1 | 7/1991 | European Pat. Off. | 471/4 |
| WO91/13071 | 9/1991 | European Pat. Off. | 403/14 |
| 0540956A1 | 10/1992 | European Pat. Off. | 471/14 |
| 0328000A2 | 2/1989 | Germany | 487/14 |
| 0384349A1 | 2/1990 | Germany | 403/4 |
| 0397060A2 | 5/1990 | Germany | 403/14 |
| WO91/13070 | 9/1991 | Germany | 403/4 |
| WO94/14798 | 7/1994 | Germany | C07D 403/14 |
| WO94/07895 | 4/1994 | WIPO | C07D 487/22 |

OTHER PUBLICATIONS

Derwent Abstract 90–132947/18; 21.10.88–DE–835842.
Derwent Abstract 92–274042/33; 90.11.20 90JP–314628.
Meier, et al., *Tetrahedron Letters,* 34:33, 5277–5280 (1993).
Wilkinson, et al., *Bichem. J.,* 294, 335–337 (1993).
Bit, et al., *J. Med. Chem.,* 36, 21–29 (1993).
Martiny–Baron, et al., *The Journal of Biological Chemistry,* 268:13, 9194–9197 (1993).
Krakowiak, et al, *SYNLETT,* 611–620, (Sep. 1993).
Mulqueen, et al., *Agents Actions,* 37, 85–89 (1992).
Davis, et al., *J. Med. Chem.,* 35, 177–184 (1992).
Davis, et al., *J. Med. Chem.,* 35, 994–1001 (1992).
Toullec, et al., *The Journal of Biological Chemistry,* 266:24, 15771–15781 (1991).
Nixon, et al., *Drugs Exptl. Clin. Res.,* 17:8, 389–393 (1991).
Davis, et al., *Tetrahedron Letters,* 31:36, 5201–5204 (1990).
Brenner, et al., *Tetrahedron Letters,* 44:10, 2887–2892 (1988).
Joyce, et al., *The Journal of Organic Chemistry,* 52:7, 1177–1186 (1987).
Buchdunger, et al., *Proc. Natl. Acad. Sci. USA,* 91, 2334–2338 (Mar. 1994).

*Primary Examiner*—David B. Springer
*Attorney, Agent, or Firm*—Steven P. Caltrider; David E. Boone

[57] ABSTRACT

The present invention discloses compounds that are highly isozyme selective protein kinase C beta-1 and beta-2 isozyme inhibitors. The present invention also provides a method of selectively inhibiting protein kinase C isozymes beta-1, and beta-2. As isozyme selective inhibitors of beta-1 and beta-2, the compounds are therapeutically useful in treating conditions associated with diabetes mellitus and its complications, as well as other disease states associated with an elevation of the beta-1 and beta-2 isozyme.

16 Claims, No Drawings

PROTEIN KINASE C INHIBITORS

BACKGROUND OF THE INVENTION

Protein kinase C (PKC) consists of a family of closely related enzymes that function as serine/threonine kinases. Protein kinase C plays an important role in cell-cell signaling, gene expression, and in the control of cell differentiation and growth. At present, there are currently at least ten known isozymes of PKC that differ in their tissue distribution, enzymatic specificity, and regulation. Nishizuka Y. *Annu. Rev. Biochem.* 58:31–44 (1989); Nishizuka Y. *Science* 258: 607–614 (1992).

Protein kinase C isozymes are single polypeptide chains ranging from 592 to 737 amino acids in length. The isozymes contain a regulatory domain and a catalytic domain connected by a linker peptide. The regulatory and catalytic domains can be further subdivided into constant and variable regions. The catalytic domain of protein kinase C is very similar to that seen in other protein kinases while the regulatory domain is unique to the PKC isozymes. The PKC isozymes demonstrate between 40–80% homology at the amino acid level among the group, however, the homology of a single isozyme between different species is generally greater than 97%.

Protein kinase C is a membrane-associated enzyme that is allosterically regulated by a number of factors, including membrane phospholipids, calcium, and certain membrane lipids such as diacylglycerols that are liberated in response to the activities of phospholipases. Bell, R. M. and Burns, D. J., *J. Biol. Chem.*, 266:4661–4664 (1991); Nishizuka, Y. *Science* 258: 607–614 ,(1992). The protein kinase C isozymes, alpha, beta-1, beta-2 and gamma, require membrane phospholipid, calcium and diacylglycerol/phorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipid for their activation.

Only one or two of the protein kinase C isozymes may be involved in a given disease state. For example, the elevated blood glucose levels found in diabetes lead to an isozyme-specific elevation of the beta-2 isozyme in vascular tissues. Inoguchi et al., *Proc. Natl. Acad. Sci. USA* 89:11059–11065 L5 (1992). A diabetes-linked elevation of the beta isozyme in human platelets has been correlated with their altered response to agonists. Bastyr III, E. J. and Lu, J. *Diabetes* 42: (Suppl 1) 97A (1993). The human vitamin D receptor has been shown to be selectively phosphorylated by protein kinase C beta. This phosphorylation has been linked to alterations in the functioning of the receptor. Hsieh et al., *Proc. Natl. Acad. Sci. USA* 88:9315–9319 (1991); Hsieh et al., *J. Biol. Chem.* 268: 15118–15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268:15847–15853 (1993).

The ubiquitous nature of the protein kinase C isozymes and their important roles in physiology provide incentives to produce highly isozyme selective PKC inhibitors. Given the evidence demonstrating linkage of certain isozymes to disease states, it is reasonable to assume that inhibitory compounds that are selective to one or two protein kinase C isozymes relative to the other PKC isozymes are superior therapeutic agents. Such compounds should demonstrate greater efficacy and lower toxicity by virtue of their specificity.

The art recognizes various classes of compounds as protein kinase C inhibitors. Some of these compounds are also known to demonstrate specificity to protein kinase C. However, very little is known regarding isozyme selectivity. Studies of the PKC-selective compound, 3-[1-(3-dimethylaminopropyl)-indol- 3-yl]-4-(1H-indol-3-yl)-1H-pyrrole-2, 5-dione, suggest a slight selectivity for the calcium dependent isozymes, but find no isozyme selectivity between alpha, beta-1, beta-2, and gamma. Toullec et al., *J. Biol. Chem.* 266:15771–15781 (1991). Martiny-Baron, et al., *J. Biol. Chem.* 268:9194–9197 (1993), tested the same compound and found slight selectivity for isozymes, alpha and beta versus delta, epsilon, and zeta. Martiny-Baron observed no differences in the selectivity between alpha and beta-1 isozymes. Wilkinson, et al., *Biochem. J.* 294: 335–337 (1993), failed to observe any high degree of isozyme selectivity and suggest only slight selectivity for the alpha isozyme and equal inhibition of beta, gamma, and epsilon for several species of bis-indolemaleimides. Therefore, despite years of research, there remains a need for therapeutically effective isozyme-selective inhibitors.

This invention provides compounds that are highly isozyme selective. The compounds selectively inhibit protein kinase C beta-1 and beta-2 isozymes. Accordingly, the present invention also provides a method of selectively inhibiting protein kinase C isozymes beta-1 and beta-2. As isozyme selective inhibitors of beta-1 and beta-2, the compounds are therapeutically useful in treating conditions associated with diabetes mellitus and its complications, as well as other disease states associated with an elevation of the beta-1 and beta-2 isozymes.

SUMMARY OF THE INVENTION

This invention provides compounds, which selectively inhibit protein kinase C beta-1 and beta-2 isozyme, of the Formula I:

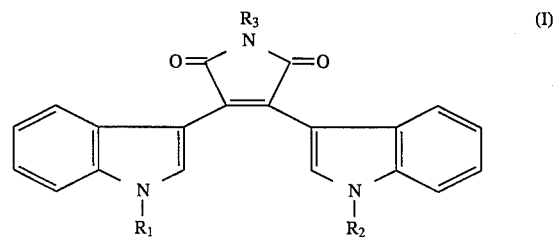

wherein:

$R_1$ is of the Formula II:

$R_2$ is hydrogen, alkyl, acyl, alkoxyalkyl, hydroxyalkyl, aminoalkyl, monoalkylaminoalkyl, dialkylaminoalkyl, acylaminoalkyl, $N_3$-alkyl, or an amino acid of the Formula (III):

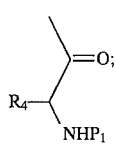
(III)

$R_3$ is H or $CH_3$;

$R_4$ is an amino acid side chain;

X is $-(CH_2)_n-NH-$, $-(CH_2)_n-O-$, phenylene—NH—, phenylene—O—, or a bond;

$P_1$ is H, alkyl, or an amino protecting group; and n is 1, 2 or 3.

The invention further provides a method of selectively inhibiting protein kinase C beta-1 and beta-2 isozyme, which comprises administering to a mammal in need of such treatment a pharmaceutically effective amount of a compound of the Formula I. As selective inhibitors, the invention further provides a method for treating diabetes mellitus, which comprises administering to a mammal in need of such treatment a pharmaceutically effective amount of a compound of the Formula I. The invention also provides pharmaceutical formulations comprising a compound off the Formula I associated with one or more pharmaceutically acceptable excipients, carriers, or diluents.

DETAILED DESCRIPTION AND PREFERRED EMBODIMENTS

As noted above, tile invention provides compounds of the Formula I which selectively inhibit isozymes of protein kinase C.

The preferred compounds are compounds of the Formula Ia:

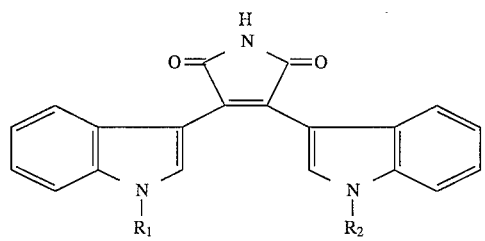
(Ia)

wherein:

$R_1$ is

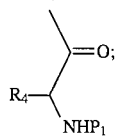

$R_2$ is amino alkyl, monoalkylamino alkyl, or dialkylamino alkyl.

Particularly preferred compounds are those wherein $R_4$ is H, $CH_3$ or

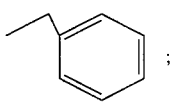
;

and $P_1$ is t-butoxycarbonyl (BOC) or benzyloxycarbonyl (CBZ).

As used herein, the term "alkyl", alone or in combinations, means a straight or branched-chain alkyl group containing from one to seven, preferably one to four, carbon atoms such as methyl, ethyl, propyl, isopropyl, butyl, secbutyl, t-butyl and pentyl. The term "$C_{1-4}$ alkyl" is an alkyl limited to one to four carbon atoms.

The term "alkoxy", alone or in combinations, is an alkyl covalently bonded to the parent moiety by a —O— linkage. Examples of alkoxy groups are methoxy, ethoxy, propoxy, isopropoxy, butoxy and t-butoxy. An alkoxyalkyl is, for example, $CH_3(CH_2)_z-O-(CH_2)_z-$ wherein z is from one to seven or preferably one to four.

The acyl moiety, alone or in combination, is derived from an alkanoic acid containing a maximum of 7, preferably a maximum of 4, carbon atoms (e.g. acetyl, propionyl or butyryl) or from an aromatic carboxylic acid (e.g. benzoyl). An acylamino is, for example, $CH_3(C=O)NH-$ (acetylamino). Likewise, an acylaminoalkyl is $CH_3(C=O)NH(CH_2)_z-$ wherein z is from one to seven or preferably one to four.

The term "amino acid side chain" represents the variable region of the naturally occurring amino acids, which are of the formulas:

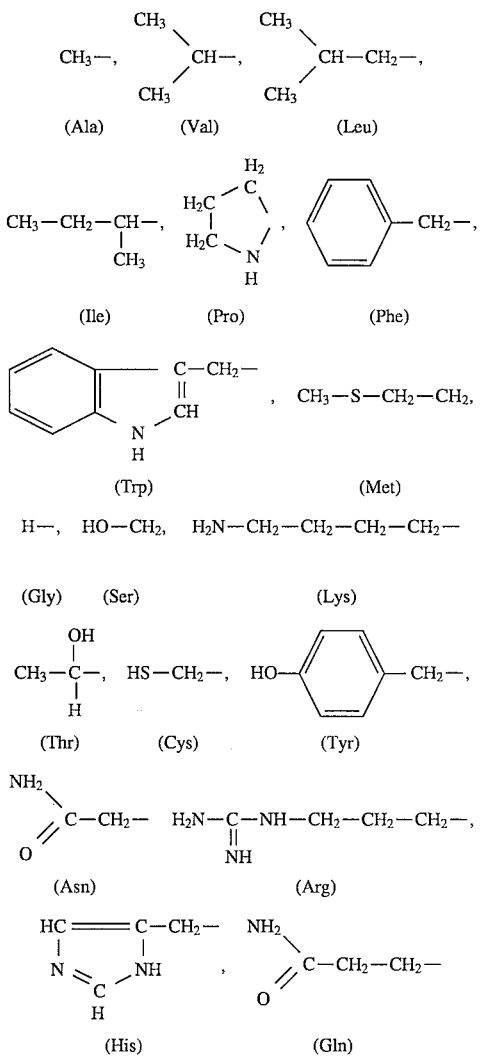

-continued

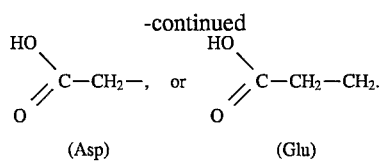

(Asp) (Glu)

The term "amino protecting group" as used herein refers to substituents commonly employed to block or protect the amino functionality. Preferred amino-protecting groups are t-butoxycarbonyl and benzyloxycarbonyl. Other amino protecting groups are found in J. W. Barton, *Protective Groups in Organic Chemistry*, J. G. W. McOmie, Ed., Plenum Press, New York, N.Y., 1973, Chapter 2, and T. W. Greene, *Protective Groups in Organic Synthesis*, John Wiley and Sons, New York, N.Y., 1981, Chapter 7, herein incorporated by reference. The related term "protected amino" defines an amino group substituted with an amino protecting group as previously discussed.

The term "pharmaceutically effective amount", as used herein, represents an amount of a compound of the invention that is capable of selectively inhibiting PKC isozyme activity in mammals. The particular dose of the compound administered according to this invention will, of course, be determined by a physician under the particular circumstances surrounding the case, including the compound administered, the route of administration, the particular condition being treated, and similar considerations. The compounds can be administered by a variety of routes including the oral, rectal, transdermal, subcutaneous, topical, intravenous, intramuscular or intranasal routes.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "isozyme selective" means the preferential inhibition of protein kinase C beta-1 or beta-2 isozymes over protein kinase C isozymes, alpha, gamma, delta, epsilon, zeta, and eta. In general, the compounds demonstrate a minimum of a eight fold differential, preferably ten fold differential, in the dosage required to inhibit PKC beta-1 or beta-2 isozymes and the dosage required for equal inhibition of the alpha protein kinase C isozyme as measured in the PKC assay. The compounds demonstrate this differential across the range of inhibition and are exemplified at tile $IC_{50}$, i.e., a 50% inhibition. Accordingly, the invention provides a method for selectively inhibiting the beta-1 or beta-2 protein kinase C isozyme. A related phrase is "selectively inhibiting protein kinase C beta-1 and beta-2 isozymes," which refers to isozyme selective inhibition. Thus, because one needs a substantially higher concentration on compound to inhibit the other protein kinase C isozymes (e.g., Example 1 discloses 50% inhibition at a concentration of 0.031 µmol/L for the beta-2 isozyme while the $IC_{50}$ with respect to the alpha protein kinase C isozyme is 1.4 µmol/L) a pharmaceutically effective dosage of the compound inhibits beta-1 and beta-2 protein kinase C isozymes with lower toxicity by virtue of their minimal inhibition of the other isozymes. Surprisingly, the bis-indolyl maleimide containing two amino acids (i.e., $R_1$ is of the Formula II and $R_2$ is of the Formula III) are yellow in appearance. This is a marked advantage because a yellow compound does not interfere with testing or monitoring of the urine of patients taking the drug.

The preparation of bis-indolemalimides of the Formula:

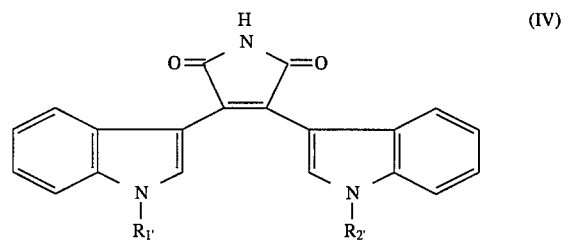

wherein $R_1'$ is hydrogen, and $R_2'$ is hydrogen, alkyl, alkoxyalkyl, hydroxyalkyl, aminoalkyl, monoalkylaminoalkyl, dialkylaminoalkyl, or acylaminoalkyl, is disclosed in U.S. Pat. No. 5,057,614 and known in the art as evidenced by EPO 397 060 (1990) and Bit et al., *J. Med. Chem.* 36:21–29 (1993). U.S. Pat. No. 5,057,614 is herein incorporated by reference.

The compounds of Formula I, are prepared by reacting a compound of Formula IV with an activated amino acid of the Formula V:

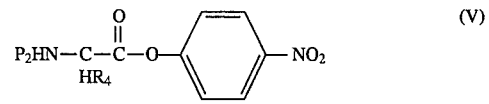

wherein $P_2$ is an amino protecting group; and $R_4$ is an amino acid side chain.

The acylation of Compound IV with the activated amino acid (Compound V) is carried out in acetonitrile in the presence of 18-crown-6 and flourine anion under basic conditions. The compounds containing an amine (e.g. Example 2) are prepared preferably with pyridine as the base for solubility purposes. The preferred base when the solubility of the substrate is not important is diisopropylethylamine. The reaction conditions and other acceptable solvents are known in the art and described in Klausner, et al., *J. Chem. Soc. Perkin I:* 607–631 (1977); and Nakagawa, et al., *J. Am. Chem. Soc.*, 105: 3709–3710 (1983).

The compounds on Formula V are commercially available or can be prepared by known methodology, e.g., Wolman Y et al, *J Chem. Soc. C:* 689 (1967); Bodanszky M et al, *J. Amer. Chem. Soc.*, 81:2504 (1959); Sakakibara S et al, *Bull. Chem. Soc. Jpn.*, 37: 1231 (1964)

When preparing the compounds of Formula I, wherein X is —$(CH_2)_n$—NH—, —$(CH_2)_n$—O—, phenylene—NH—, or phenylene—O—, the linking moiety, X, is appendaged to the bis-indolylmaleimide prior to the coupling. Thus, for example, when $R_1$ is

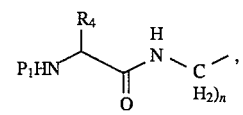

$R_1'$ is aminoalkyl. Likewise, when $R_1$ is

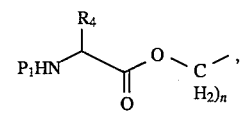

$R_1'$ is hydroxyalkyl. The coupling reaction when X is —$(CH_2)_n$—O— or phenylene—O— may be alternatively carried out with dicyclohexylcarbodiimide and 4-dimethylaminopyridine under standard coupling conditions known in the art.

By virtue of their acidic moieties, the compounds of Formula I include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

Because of the basic moiety, the compounds of Formula I can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, parabromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, hepnanoate, propiolate, oxalate, malonate, succinate, suberate, sebacate, fumarate, maleate, 2-butyn-1,4-dioate, 3-hexyn-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, maleate, tartrate, methanesulfonate, propanesulfonate, naphthalene-1-sulfonate, naphthalene-2-sulfonate, mandelate and the like salts.

In addition to pharmaceutically-acceptable salts, other salts are included in the invention. They may serve as intermediates in the purification of compounds or in the preparation of other salts, or are useful for the identification, characterization or purification.

The pharmaceutically acceptable salts of compounds of Formula I can also exist as various solyates, such as with water, methanol, ethanol, dimethylformamide, ethyl acetate and the like. Mixtures of such solyates can also be prepared. The source of such solvate can be from the solvent of crystallization, inherent in the solvent of preparation or crystallization, or adventitious to such solvent. Such solvates are within the scope of the present invention.

It is recognized that various stereoisomeric forms of the compounds of Formula I may exist; for example, $R_1$ introduces a chiral carbon atom. The compounds are normally prepared as racemates and can conveniently be used as such, but individual enantiomers can be isolated or synthesized by conventional techniques if so desired. Such racemates and individual enantiomers and mixture thereof form part of the present invention.

As previously noted, the compounds of the present invention are potent, beta-1 and beta-2 isozyme selective PKC inhibitors. As such, they are useful in the treatment of conditions associated with diabetes mellitus and its complications, as well as other disease states associated with an elevation of the beta-1 and beta-2 isozymes.

Protein kinase C beta-1 and beta-2 has been linked to diabetes. Inoguchi et al., *Proc. Natl. Acad. Sci. USA* 89: 11059–11065 (1992). Excessive activity of protein kinase C has been linked to insulin signaling defects and therefore to the insulin resistance seen in Type II diabetes. Karasik, A. et al., *J. Biol. Chem.* 265:10226–10231 (1990); Chen, K. S. et al., *Trans. Assoc. Am. Physicians* 104:206–212 (1991); Chin, J. E. et al., *J. Biol. Chem.* 268:6338–6347 (1993). Further, studies have demonstrated a marked increase in protein kinase C activity in tissues known to be susceptible to diabetic complications when exposed to hyperglycemic conditions. Lee, T.-S. et al., *J. Clin. Invest.* 83:90–94 (1989); Lee, T.-S. et al., *Proc. Natl. Acad. Sci. USA* 86:5141–5145 (1989); Craven, P. A. and DeRubertis, F. R. *J. Clin. Invest.* 83: 1667–1675 (1989); Wolf, B. A. et al., *J. Clin. Invest.* 87:31–38 (1991); Tesfamariam, B. et al., *J. Clin. Invest.* 87:1643–1648 (1991); Bastyr III, E. J. and Lu, J., *Diabetes* 42: (Supp 11) 97A (1993).

The ability of the compounds of the present invention to selectively inhibit protein kinase C beta-1 and beta-2 isozyme was determined in the PKC Enzyme assay.

PKC Enzyme Assay

PKC enzymes=alpha, beta 1, beta II, gamma, delta, epsilon, eta and zeta.

Assay components in a total volume of 250 μL are the following:

Vesicles consisting of 120 μg/mL phosphatidylserine (Avanti Polar Lipids) and sufficient diacylglycerol (Avanti Polar Lipids) to activate the enzyme to maximum activity in 20 mM HEPES buffer (Sigma, St. Louis, Mo.), pH 7.5, 940 μM calcium chloride (Sigma, St. Louis, Mo.) for assaying the alpha, beta I, beta II and gamma enzyme only, 1 mM EGTA for all the enzymes, 10 mM magnesium chloride (Sigma, St. Louis, Mo.) and 30 μM (gamma-32P) ATP (DuPont). For all the enzymes either histone type HL (Worthington) or myelin basic protein is used as substrate. The assay is started by addition of protein kinase C enzyme incubated at 30° C. for 10 minutes and stopped by adding 0.5 mL of cold trichloroacetic acid (Amresco) followed by 100 μL of 1 mg/mL bovine serum albumin (Sigma, St. Louis, Mo.). The precipitate is collected by vacuum filtration on glass fiber filters employing a TOMTEC™ filtration system and quantified by counting in a beta scintillation counter.

Using the methodoloy described, representative compounds were evaluated and were found to have an $IC_{50}$ value with respect to the beta-1 and beta-2 isozyme of below 10 μm. The compounds are isozyme selective, i.e., the compounds preferentially inhibit protein kinase C beta-1 and beta-2 isozyme over the protein kinase C isozymes, alpha, gamma, delta, epsilon, zeta, and eta. In general, the compounds demonstrate a minimum of an eight fold differential in the dosage required to inhibit PKC beta-1 or beta-2 isozyme and the dosage required for equal inhibition of the alpha protein kinase C isozyme as measured in this assay. Therefore, as selective inhibitors of PKC isozyme beta-1 and beta-2, the compounds are useful in the treatment of conditions in which PKC beta has demonstrated a role in the pathology, in particular, diabetes mellitus and its complications.

The following examples are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, N,N-dimethylformamide, palladium on charcoal, diisobutylaluminum hydride, acetonitrile, and tetrahydrofuran are abbreviated M.Pt., NMR, MS, HPLC, DMF, Pd/C, DIBAL, ACN and THF, respectively. The terms "NMR" and "MS" indicate that the spectrum was consistent with the desired structure.

EXAMPLE 1

3-[1-(3-azidopropyl)-3-indolyl]-4-[(1-N-'BOC )-glycine-3 indolyl]-1H-pyrrol-2,5-dione 3-[1-(3-azidopropyl)-3-indolyl]-4-[3-indolyl]-1H-pyrrol-2,5-dione (0.20 g, 0.49 mol, 1 eq) was transferred to an oven dried 50 mL round bottom flask equipped with a stir bar, septum, and $N_2$ balloon. The red solid was dissolved in about 25 mL of anhydrous acetonitrile (delivered via canula) and stirring started. To the red solution was added (N-'B-OC)glycine, p-nitrophenyl ester (0.22 g, 0.74 mmol, 1.5 eq), 18-crown-6 (0.13 g, 0.49 mmol, 1 eq), and N,N-diisopropylethylamine (0.08 g, 0.61 mmol, 1.25 eq, 0.11 mL), and potassium fluoride (0.06 g, 0.98 mmol, 2 eq) with vigorous stirring. This red solution was allowed to stir under a $N_2$ atmosphere for 5 days.

TLC (50% EtOAc in hexanes) of the reaction indicated total loss of starting materials. The reaction was diluted with 100 mL of EtOAc, transferred to a separatory funnel, washed with water, and brine. The organic layer was dried over $MgSO_4$. The solvent was removed in vacuo to obtain a red oil. This oil was purified by silica flash chromatography using 37.5% EtOAc in hexanes as the mobile phase to give 0.2055 g of an orange solid.

NMR, MS

Elemental Analysis: Theory: C 63.48 N 17.27 H 5.15; Found: C 63.53 N 16.28 H 5.64.

EXAMPLE 2

3-[1-(3-N,N'-dimethylaminopropyl)-3-indolyl]-4-[(1-N-'BOC)-glycine-3-indolyl]-1H-pyrrol-2,5-dione 3-[1-(3-N,N'-dimethylaminopropyl)-3-indolyl]-4-[3 -indolyl]-1H-pyrrol-2,5-dione (0.05 g, 0.12 mmol, 1 eq) was transferred to a 100 mL round bottom flask equipped with a stir bar, septum, and $N_2$ balloon. Anhydrous acetonitrile (70 mL) was delivered via canula followed by pyridine (0.05 g, 0.62 mmol, 5 eq, 0.05 mL) via syringe. The resulting orange suspension was heated to 50° C. for 60 minutes to help solubilize the compound. After 60 min, (N-'BOC)glycine, p-nitrophenyl ester (0.07 g, 0.24 mmol, 2 eq), 18-crown-6 (0.06 g, 0.24 mmol, 2 eq), and dry potassium fluoride (0.03 g, 0.48 mmol, 4 eq) were added as solids with vigorous stirring. The resulting yellow/orange solution was allowed to stir at room temperature under an atmosphere of $N_2$ for 48 hours. MS (FD in MeOH): MW-569.67; m/z 570 (MH+)P

EXAMPLE 3

3,4-Bis[(1-N-'BOC)-phenylalanine-3-indolyl]-1H-Pyrrol-2,5-dione 3,4-Bis[3-indolyl]-1H-pyrrol-2,5-dione (0.165 g, 0.5 mmol, 2 eq) was transferred to an oven dried 50 mL round bottom flask equipped with stir bar, septum, and $N_2$ balloon. Anhydrous acetonitrile (25 mL) was added via canula and stirring started to produce a red solution. (N-'BOC)phenylalanine, p-nitrophenyl ester (0.67 g, 1.75 mmol, 3.5 eq), 18-crown-6 (0.13 g, 0.5 mmol, 2 eq), and diisopropylethylamine (0.16 g, 1.25 mmol, 2.5 eq, 0.22 mL) were then added to the solution with vigorous stirring. When everything had dissolved, anhydrous potassium fluoride (0.12 g, 2 mmol, 4 eq) was added as a solid. The solution was allowed to stir under nitrogen at room temperature overnight.

After 16 hours of stirring, TLC (50% EtOAC in hexanes) showed loss of starting material. The yellow solution was transferred to a separatory funnel with ~150 mL of EtOAc. This solution was washed with water and brine. The organic layer was collected and then dried over $MgSO_4$. The solvent was removed to give a bright yellow/orange residue. This residue was purified by silica flash chromatography using 37.5% EtOAc in hexanes as the mobile phase to give a bright yellow film after the solvent was removed. HPLC of this solid still showed some impurities so the product was purified using the gel permeation hydrophobic columns with $CHC_{13}$ as the mobile phase to give 229 mg of a bright yellow solid. NMR, MS (FD in MeOH): MW-821.94; m/z 822 (MH+).

EXAMPLE 4

3-[1-(3-acetamidepropyl)-3-indolyl]-4-[(1-N-'BOC)-glycine-3-indolyl]-1H-pyrrol-2,5-dione 3-[1-(3-azidopropyl)-3-indolyl]-4-[(1-N-'BOC)-glycine-3-indolyl]-1H-pyrrol-2,5-dione (80 mg, 0.14 mmol, 1 eq) was dissolved in ethyl acetate in a 100 mL round bottom flask equipped with a stir bar and 14/22 adapter. Lindlar's catalyst (catalytic, 8 mg) and acetic anhydride (40 mg, 0.39 mmol, 3 eq) were added with vigorous stirring to the red solution. A hydrogen balloon was placed on top of the flask. The flask was then evacuated and filled with hydrogen 3 times to remove dissolved oxygen from the solution. The reaction was allowed to stir at room temperature under the hydrogen atomosphere overnight.

After stirring overnight, TLC (50% EtOAc in hexanes) of the reaction indicated loss of the starting material. The reaction was filtered through a pad of celite to remove the hydrogenation catalyst. The red solution was transferred to a separatory funnel and diluted with ~100 mL of EtOAc. The organic layer was washed with water and brine and then collected and dried over $MgSO_4$. The solvent was removed to give an orange residue. This residue was purified using size exclusion gel permeation columns using chloroform as the mobile phase to give 52.4 mg of an orange residue. MS (FD in MeOH): MW-583.65; m/z 584 (MH+),426 (M+-amino acid).

| Ex. | $IC_{50}$ (μm) | | | | | | | |
|---|---|---|---|---|---|---|---|---|
| | α | β1 | β2 | γ | δ | ε | ζ | η |
| 1 | 1.4 | 0.26 | 0.031 | 19 | 4.6 | NA | 100 | 2.6 |
| 2 | 2.3 | 0.15 | 0.04 | 2.6 | 2.9 | 6.1 | 45 | 0.37 |
| 3 | 83 | 1 | 2.6 | >100 | >100 | NA | >100 | NA |

NA - data not available

The compounds of Formula I are formulated prior to administration. A pharmaceutical formulation comprises a compound of the Formula I with one or more pharmaceutically acceptable excipients, carriers, or diluents. Pharmaceutical formulations are prepared by known procedures using well known and readily available ingredients. In making the compositions, the active ingredient will usually be mixed with a carrier, or diluted by a carrier, or enclosed within a carrier, which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 5 to about 500 mg, more usually about 25 to about 300 mg, of the active ingredient. However, it will be understood that the therapeutic dosage administered will be determined by the physician in the light of the relevant circumstances including the condition to be treated, the choice of compound to be administered and the chosen route of administration, and therefore %he above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, the compounds of the present invention may be administered topically. Topical formulations are ointments, creams, and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances that can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added to an amount to achieve the desired concentration.

Gels comprise a base selection from an oleaginous base, water, or an emulsion-suspension base, such as aforedescribed. To the base is added a gelling agent that forms matrix in the base increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation of invention is not critical; the concentration should only be a range sufficient to permit ready application of the formulation to the an affected tissue area in an amount that will deliver the desired amount of compound. The customary amount of topical formulation to be applied to an affected tissue will depend upon an affected tissue size and concentration of compound in the formulation. Generally, the formulation will be applied to the an affected tissue in an amount affording from about 1 to about 500 µg compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The following formulation examples are illustrative only and are not intended to limit the scope of the invention in any way.

FORMULATION 1

Hard gelatin capsules acre prepared using the following ingredients:

|  | Quantity (mg/capsule) |
|---|---|
| Active ingredient | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

|  | Quantity (mg/capsule) |
|---|---|
| Active ingredient | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Quantity (mg/capsule) |
|---|---|
| Active ingredient | 0.25 |
| ethanol | 29.75 |
| Propellant 22 | 70.00 |
| (chlorodifluoromethane) Total | 100.00 |

The active compound is mixed with ethanol. The mixture is added to a portion of the Propellant 22, cooled to −30° C.

and transferred to a filling device. The required amount is then fed to a stainless steel container and diluted with the remainder of the propellant. The valve units are then fitted to the container.

FORMULATION 4

Tablets each containing 60 mg of active ingredient are made as follows:

|  | Quantity (mg/capsule) |
| --- | --- |
| Active ingredient | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

|  | Quantity (mg/capsule) |
| --- | --- |
| Active ingredient | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of active ingredient may be made as follows:

|  | Quantity (mg/capsule) |
| --- | --- |
| Active ingredient | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

|  | Quantity (mg/capsule) |
| --- | --- |
| Active ingredient | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

|  | Quantity (mg/capsule) |
| --- | --- |
| Active ingredient | 250 mg |
| isotonic saline | 1000 mg |

The solution of the above ingredients is administered intravenously at a rate of 1 ml per minute to a subject in need of treatment.

We claim:

1. A compound of the formula:

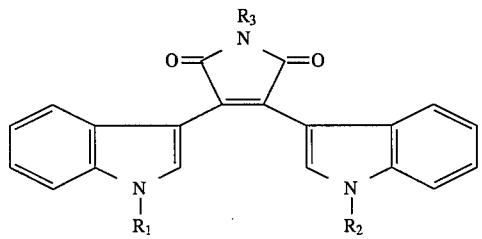

wherein:

$R_1$ is of the formula:

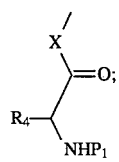

$R_2$ is hydrogen, alkyl, $R_3$ is H or $CH_3$;

$R_4$ is an amino acid side chain;

X is —$(CH_2)_n$—NH—, —$(CH_2)_n$—O—, phenylene—NH—, phenylene—O—, or a bond;

$P_1$ is H, alkyl, or an amino protecting group; and n is 1, 2 or 3;

or a pharmaceutically acceptable salt or solvate thereof.

2. A compound off claim 1 wherein X is a bond.

3. A compound off claim 2 wherein $R_3$ is H.

4. A compound of claim 3 of the formula:

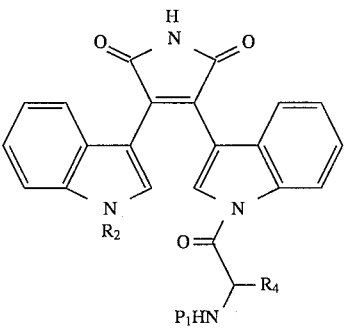

wherein $R_2$ is hydrogen or alkyl;

$R_4$ is H, $CH_3$,

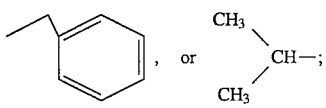

and $P_1$ is H, t-butoxycarbonyl, or benzyloxycarbonyl.

5. A method for treating diabetes mellitus, which comprises administering to a mammal in need of such treatment a pharmaceutically effective amount of a compound of claim 1.

6. A method for treating diabetes mellitus, which comprises administering to a mammal in need of such treatment a pharmaceutically effective amount of a compound of claim 2.

7. A method for treating diabetes mellitus, which comprises administering to a mammalin need of such treatment a pharmaceutically effective amount of a compound of claim 3.

8. A method for treating diabetes mellitus, which comprises administering to a mammal in need of such treatment a pharmaceutically effective amount of a compound of claim 4.

9. A method of selectively inhibiting protein kinase C beta-1 and beta-2 isozyme, which comprises administering to a mammal in need of such treatment a pharmaceutically effective amount of a compound of claim 1.

10. A method of selectively inhibiting protein kinase C beta-1 and beta-2 isozyme, which comprises administering to a mammal in need of such treatment a pharmaceutically effective amount of a compound of claim 2.

11. A method of selectively inhibiting protein kinase C beta-1 and beta-2 isozyme, which comprises administering to a mammal in need of such treatment a pharmaceutically effective amount of a compound of claim 3.

12. A method of selectively inhibiting protein kinase C beta-1 and beta-2 isozyme, which comprises administering to a mammal in need of such treatment a pharmaceutically effective amount of a compound of claim 4.

13. A pharmaceutical formulation comprising a compound of claim 1 with one or more pharmaceutically acceptable excipients, carriers, or diluents.

14. A pharmaceutical formulation comprising a compound of claim 2 with one or more pharmaceutically acceptable excipients, carriers, or diluents.

15. A pharmaceutical formulation comprising a compound of claim 3 with one or more pharmaceutically acceptable excipients, carriers, or diluents.

16. A pharmaceutical formulation comprising a compound of claim 4 with one or more pharmaceutically acceptable excipients, carriers, or diluents.

* * * * *

UNITED STATES PATENT AND TRADEMARK OFFICE
CERTIFICATE OF CORRECTION

PATENT NO. : 5,481,003
DATED : January 2, 1996
INVENTOR(S) : James R. Gilling; Michael R. Jirousek It is certified that error appears in the above-indentified patent and that said Letters Patent is hereby corrected as shown below:

Column 15, line 11    "off" should appear as --of--

Column 15, line 12    "off" should appear as --of--

Column 16, line 5    "mammalin" should appear as --mammal in--

Signed and Sealed this

Twenty-fourth Day of December, 1996

Attest:

BRUCE LEHMAN

Attesting Officer    Commissioner of Patents and Trademarks